United States Patent [19]
Kanner et al.

[11] Patent Number: 5,868,755
[45] Date of Patent: Feb. 9, 1999

[54] SHEATH RETRACTOR MECHANISM AND METHOD

[75] Inventors: Rowland W. Kanner, Guntersville; Larry Lee Young, Arab, both of Ala.

[73] Assignee: Atrion Medical Products, Inc., Arab, Ala.

[21] Appl. No.: 784,745

[22] Filed: Jan. 16, 1997

[51] Int. Cl.[6] .................................................. A61F 11/00
[52] U.S. Cl. ........................................ 606/108; 606/198
[58] Field of Search ...................... 606/1, 108, 191–200; 604/157, 171, 164, 264

[56] References Cited

U.S. PATENT DOCUMENTS

| | | | |
|---|---|---|---|
| 3,835,854 | 9/1974 | Jewett | 604/159 |
| 4,917,094 | 4/1990 | Lynch et al. | 604/164 |
| 5,346,498 | 9/1994 | Greelis et al. | 606/108 |
| 5,391,172 | 2/1995 | Williams et al. | 606/108 |
| 5,409,478 | 4/1995 | Gerry et al. | 606/108 |
| 5,601,568 | 2/1997 | Chevillon et al. | 606/108 |

Primary Examiner—Glenn K. Dawson
Attorney, Agent, or Firm—Trexler, Bushnell, Giangiorgi & Blackstone, Ltd.

[57] ABSTRACT

An actuating mechanism and method for sequentially translating a sheath member relative to an elongate member such as a balloon catheter movably inserted through the sheath includes a coupling structure constructed to enable selectively coupling or uncoupling of a drive member to the sheath member in order to drive translation of the coupled sheath member in one or more translation increments and to enable uncoupling of the drive member following each of said increments of retraction. In a particularly beneficial method of sheath retraction from a portion of an angioplasty balloon catheter on which a stent is mounted, the method includes coupling a drive structure to the sheath and driving translation of the coupled sheath relative to the catheter to expose the stent-mounted portion of the catheter, and then repeating the translational drive of the coupled sheath to further translate the sheath and expose a further incremental portion of the catheter, in order to produce sequential one-way movement of the sheath in controlled increments to attain exposure of the balloon catheter and the stent mounted thereon without disturbing its position.

41 Claims, 10 Drawing Sheets

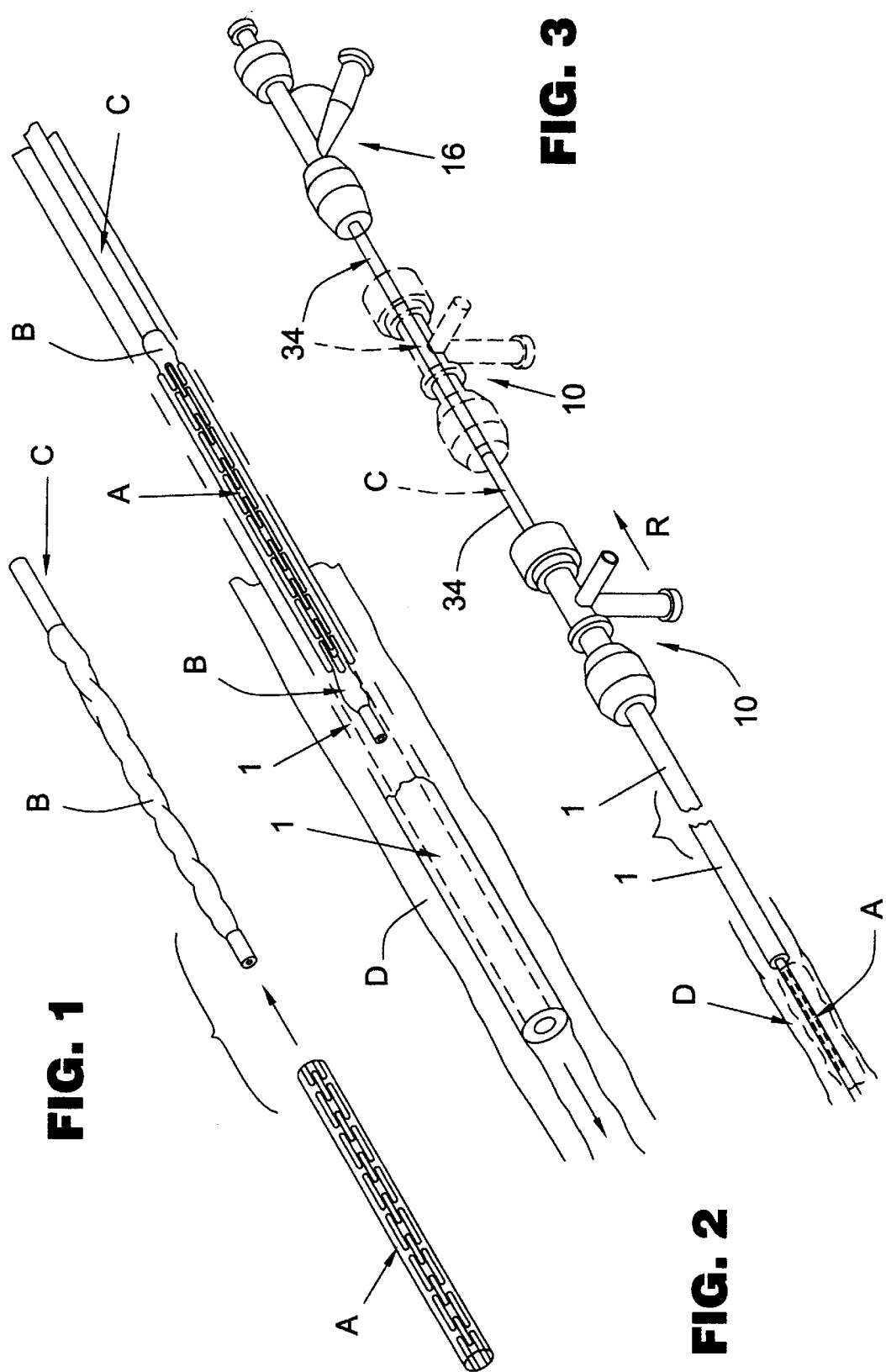

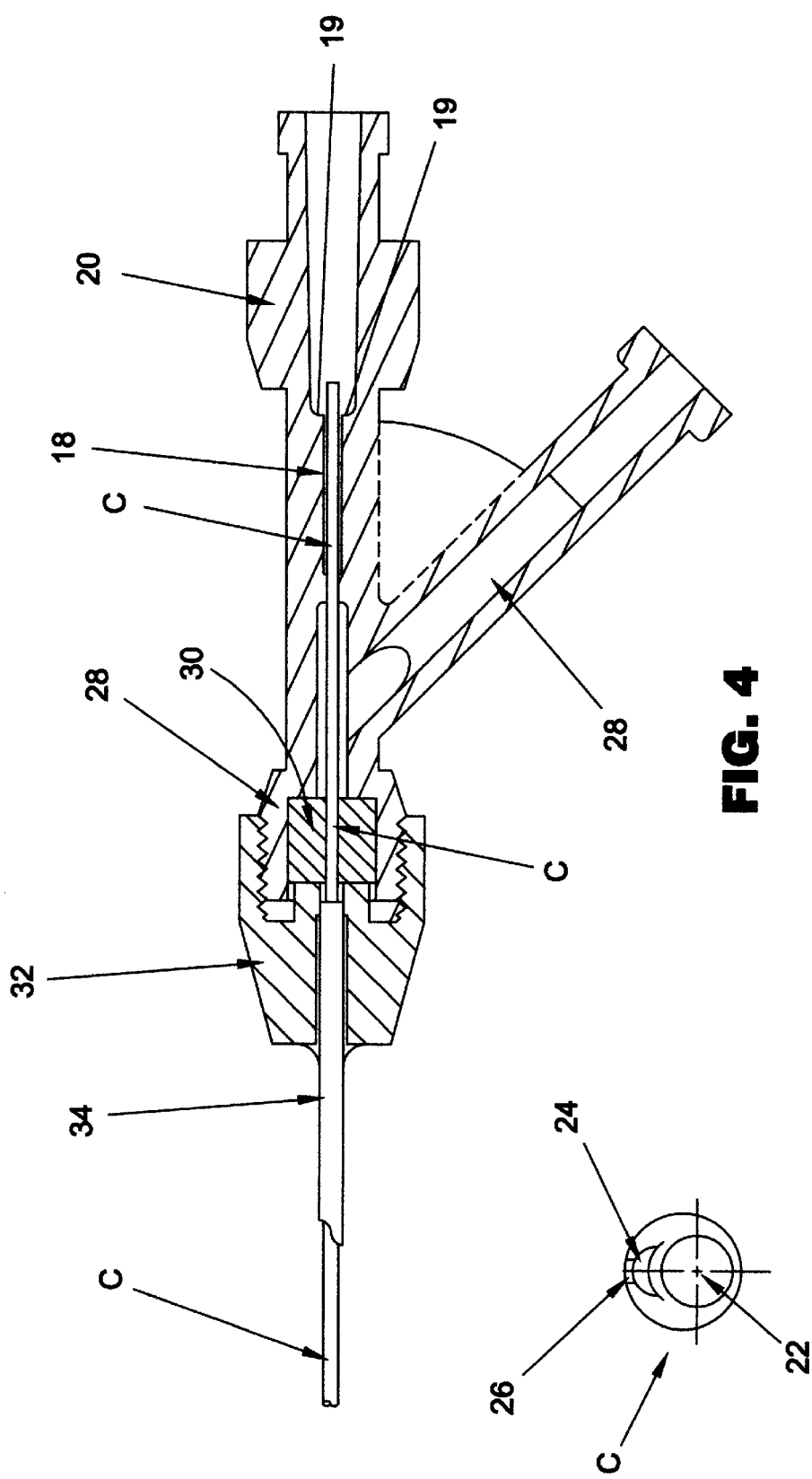

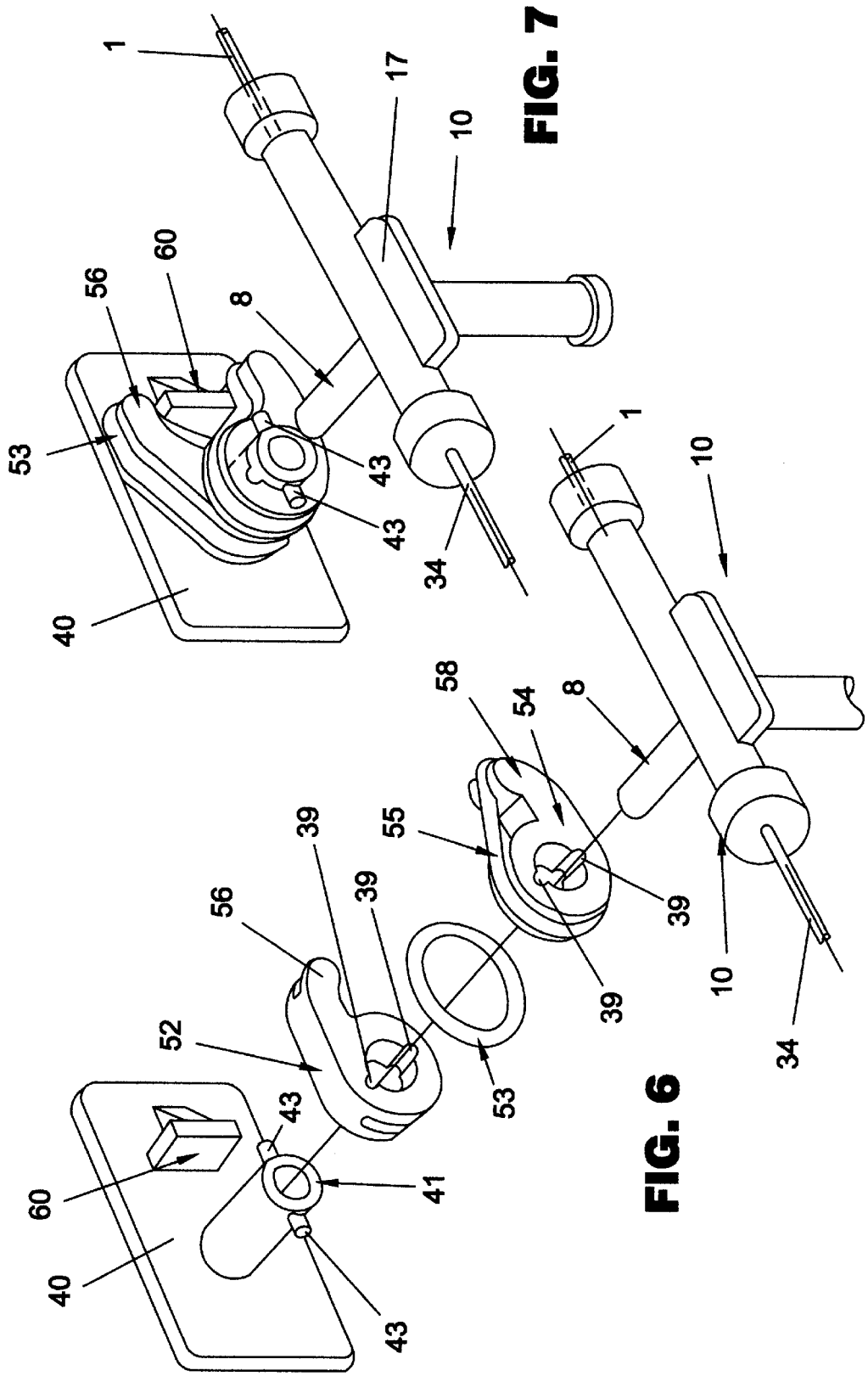

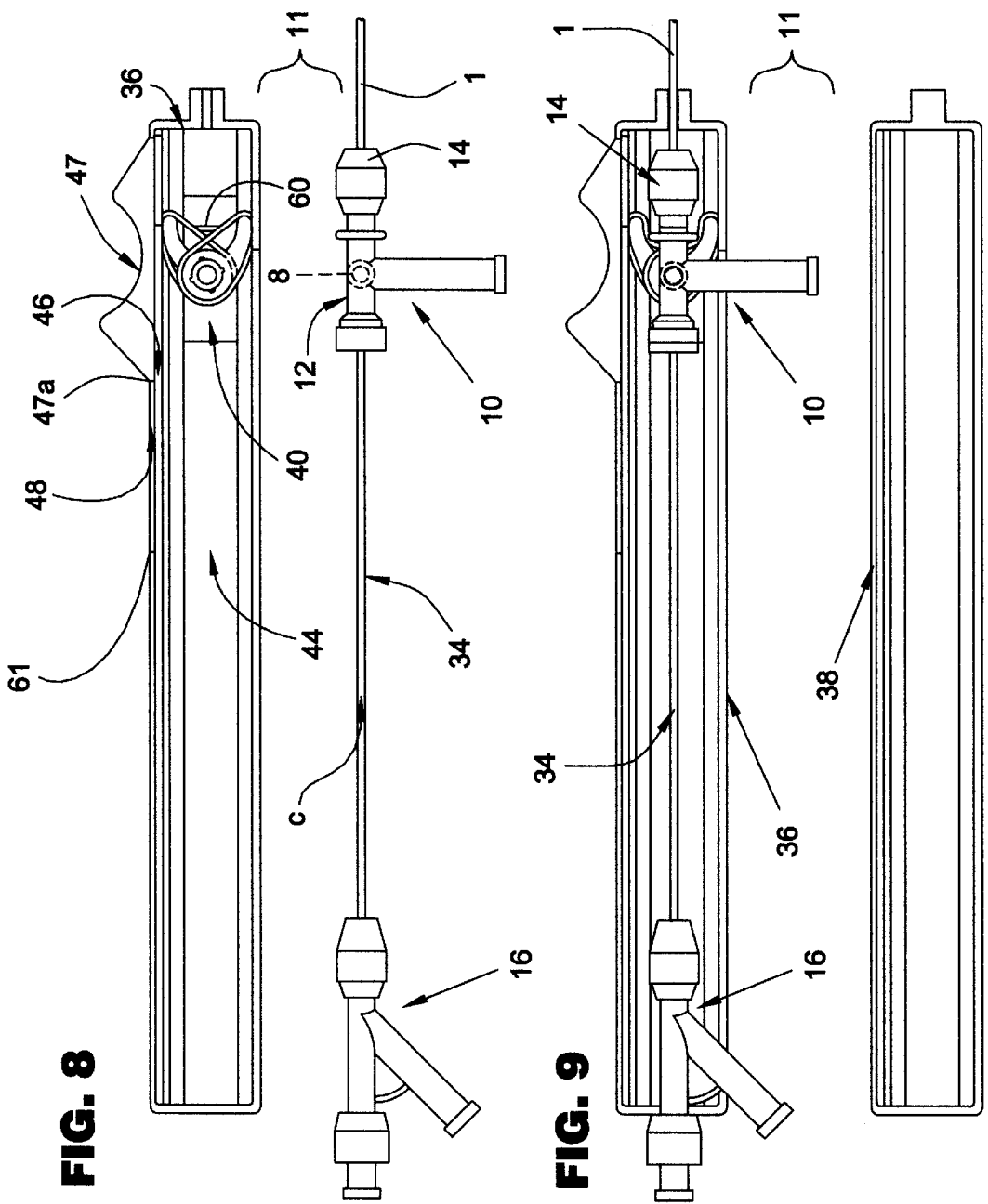

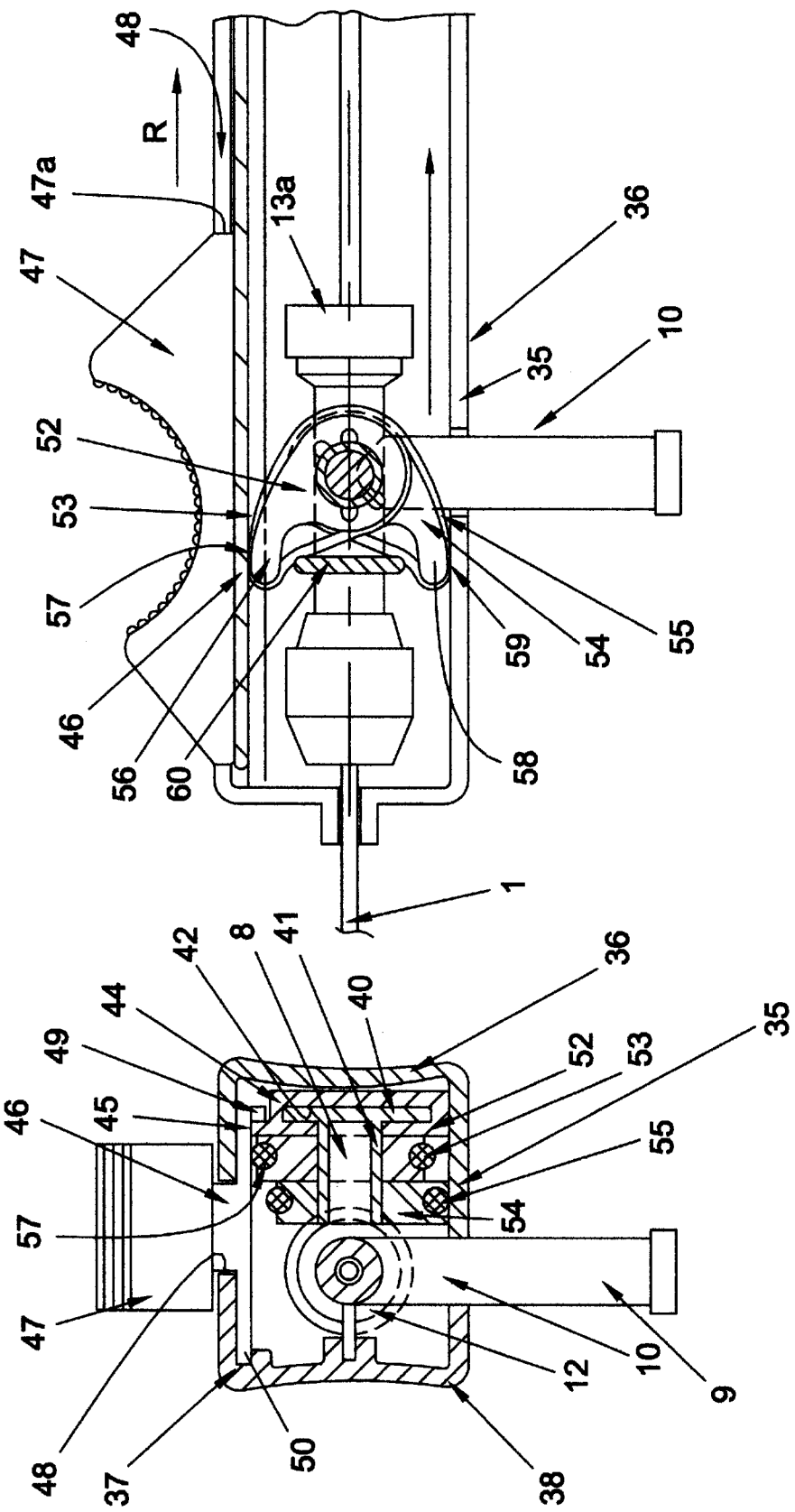

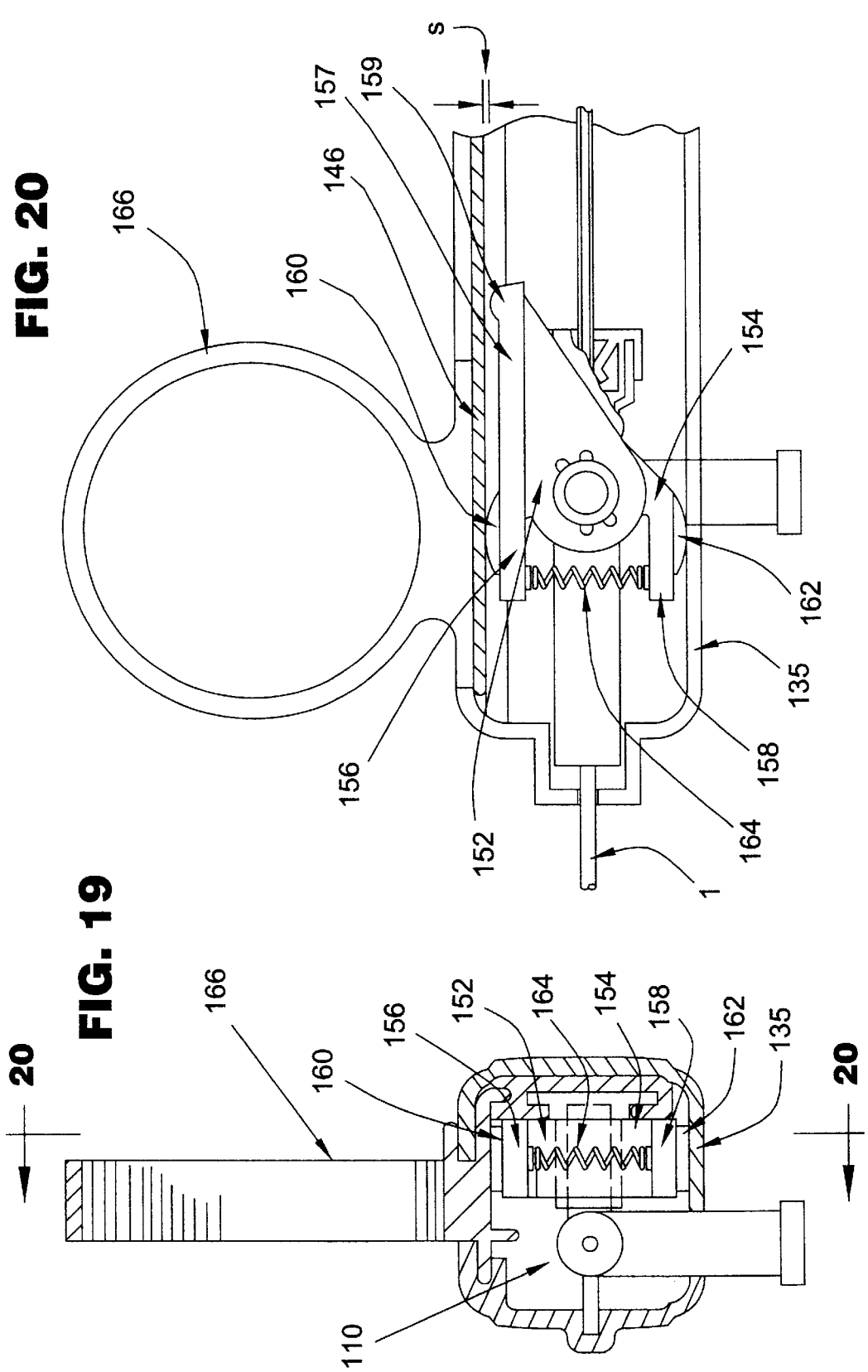

5,868,755

SHEATH RETRACTOR MECHANISM AND METHOD

BACKGROUND

The present invention relates to surgical angioplasty balloon instruments and procedures. More particularly, the present invention relates to an instrument, mechanism and procedure for retracting or withdrawing a protective sheath surrounding a balloon catheter having an angioplasty stent applied thereto, prior to implanting of the stent, following retraction of the protective sheath.

In order to improve the effectiveness of vascular angioplasty in relieving blockage or repairing cardiovascular damage, stainless steel mesh stents of tubular configuration have been developed for implantation into the vascular wall of a patient. The stent is introduced by a balloon catheter, the stent being carried by the expandable balloon portion of the catheter, which is expanded to attain expansion and implantation of the stent. The catheter and stent are protected by a surrounding sheath which is maintained in place over the stent during introduction to the implantation site, and which is then retracted to expose the stent prior to the expansive implantation procedure. The protective sheath prevents any potential slippage of the stent relative to the deflated balloon before and during the introduction and location of the stent at the implantation site. In addition, the sheath will cover the stent as it passes through the patient's vascular system, such that mesh material or edges of the stent are covered during introduction, which edges or portions could lead to abrasion or damage of the vascular tissue during introduction. Once the precise implantation site has been reached, the protective sheath must be carefully retracted to expose the stent for expansion and implantation. Unintended re-advancement of the sheath can cause its forward end to catch on the stent and produce slippage on a deflated balloon, resulting in displacement of the stent from the correct vascular implantation site. These and other disadvantages are eliminated by the mechanism, instruments and method in accordance with the present invention.

SUMMARY OF THE INVENTION

In accordance with the present invention, an actuating mechanism and method for sequentially translating a sheath member relative to an elongate member such as a balloon catheter movably inserted through the sheath comprises a coupling structure constructed to enable selectively coupling or uncoupling of a drive member to the sheath member in order to drive translation of the coupled sheath member in one or more translation increments and to enable uncoupling of the drive member following each of said increments of retraction.

In a particularly beneficial method of sheath retraction from a portion of an angioplasty balloon catheter on which a stent is mounted, the method comprises coupling a drive structure to the sheath and driving translation of the coupled sheath relative to the catheter to expose the stent-mounted portion of the catheter, and then repeating the translational drive of the coupled sheath to further translate the sheath and expose a further incremental portion of the catheter, in order to produce sequential one-way movement of the sheath in controlled increments to attain exposure of the balloon catheter and the stent mounted thereon.

In preferred embodiments of an actuating instrument and method in accordance with the invention, the drive member is movable in order to produce retractive movement of a support structure which is connected to the sheath, in a first movement direction of the drive member. Thereafter, when the drive member is moved in the reversed direction to return the drive member to its initial position, the drive member is uncoupled from or deactivated with respect to the support structure, so that the sheath is not moved in a direction opposite its retractive movement. The drive member is then recoupled to or actively engaged with the support structure and then moved in the first direction to produce a second increment of retraction of the sheath member, so that the sheath member can only be moved in a single direction which retracts the sheath from the end of the catheter, to ensure that the forward end of the sheath cannot move in the opposite direction to deflect or dislodge the stent from the correctly exposed position on the deflated balloon end of the catheter for subsequential implantation in the precisely located site along the vascular wall. The increments of sheath retraction are uniform in displacement and coextensive with the surgeon's retraction stroke of the drive member.

The preferred coupling structure of the mechanism and instrument employs frictional gripping members which releasibly grip the drive member on the retraction stroke but automatically release on the return stroke, to ensure the one-way retractive displacement of the sheath in smooth translation without vibration so that the precise vascular positioning of the catheter and stent are maintained undisturbed.

BRIEF DESCRIPTION OF THE DRAWINGS

FIG. 1 is a somewhat schematic perspective view of a vascular stent device prior to engagement to an angioplasty balloon catheter device;

FIG. 2 is an assembled view of the stent mounted on the balloon catheter, as shown in FIG. 1, with a sheath over the stent, and the entire assembly disposed within a vascular pathway;

FIG. 3 is a perspective view of the stent mounted on the balloon catheter shown in FIG. 1 and partially covered by a protective sheath with both the sheath and the balloon catheter connected to portions of one embodiment of a sheath retraction instrument in accordance with the present invention;

FIG. 4 is a vertical sectional view of a support fitting portion for the balloon catheter mounted in the portion of the sheath retraction instrument shown in FIG. 3;

FIG. 4a is a sectional view of the catheter shown in FIGS. 1–4 illustrating the dual lumens incorporated in the catheter;

FIG. 6 is an exploded perspective view of the drive coupling mechanism portion of the instrument shown in FIG. 5;

FIG. 7 is a partially assembled view of the mechanism shown in FIG. 6;

FIG. 8 is a partially assembled side view of the instrument shown in FIG. 5;

FIG. 9 is a further assembled view of the partially assembled instrument shown in FIG. 8;

FIG. 10 is a partially sectional end view of the drive mechanism portion of the instrument shown in FIGS. 5–9;

FIG. 11 is a partially sectional side view of the instrument portion shown in FIG. 10;

FIGS. 19 and 20 are partially sectional views of a second embodiment of a drive mechanism portion of a sheath retractor instrument in accordance with the present invention.

DETAILED DESCRIPTION OF THE ILLUSTRATED EMBODIMENTS

Referring to FIGS. 1–3, a balloon-expandable "stent" A having a conventional, stainless steel, slotted tubular mesh configuration is shown in an unexpanded or intermediate condition in FIG. 1. The stent A is slipped over and onto a deflated angioplasty balloon B of catheter unit C. Thereafter, the stent is compressed slightly into uniform cohesive purchase or engagement on the deflated balloon B. Preferably compression is achieved using a fluid compression instrument as described in pending U.S. patent application Ser. No. 08/567,136, filed Dec. 4, 1995 entitled "STENT COMPRESSION INSTRUMENT", now abandoned, the specification, drawings and disclosure of which is incorporated by reference herein for complete discussion of stent securement.

In order to prevent any dislodgement or slippage of the stent A from the deflated balloon before or during an angioplasty procedure, the compressed stent/balloon unit is disposed or inserted within a protective tubular sheath 1 as shown in FIGS. 2 and 3. The sheath 1 also prevents the mesh material and any edge portion of the stent A from abrading or damaging any vascular wall tissue during insertion and movement of the stent/balloon through the vessel lumen in the angioplasty implantation procedure. Once the sheath covered stent/balloon/catheter has been fed through the lumen of the vascular vessel D so that the stent A is positioned at a previously determined site for angioplasty dilation, the sheath 1 is then retracted, as shown in FIG. 3, in accordance with method and device of the present invention. Retraction of the sheath exposes the stent such that the balloon catheter can be inflated to attain dilation and vascular implantation of the stent, in a known manner.

The present invention provides a novel and easily operated instrument that can be employed by the vascular surgeon for withdrawing the protective sheath disposed over the balloon catheter and stent in a controlled fashion. The sheath retractor of the present invention provides for smooth, low friction actuation, and most importantly, the activation is positive and in but one direction on a one-to-one basis with operation of the instrument. This allows the vascular surgeon to sense and control the slow retraction of the stent, without causing any whipping of the catheter end. Also, since the drive mechanism of the present invention has a positive, no backlash retraction and withdrawal of the sheath, there is no danger that operation of the operating, slide mechanism will result in unwanted forward movement of the sheath which could lead to inadvertent movement or dislodgement of the stent from its end of the balloon catheter. Further, the operating mechanism is smooth and low friction, unlike a ratchet-type mechanism which are noisy, produce vibrations, and do not provide tactile monitoring and feedback. The control and tactile feedback with the instrument of the present invention to be described hereinafter is excellent.

Figure 5:
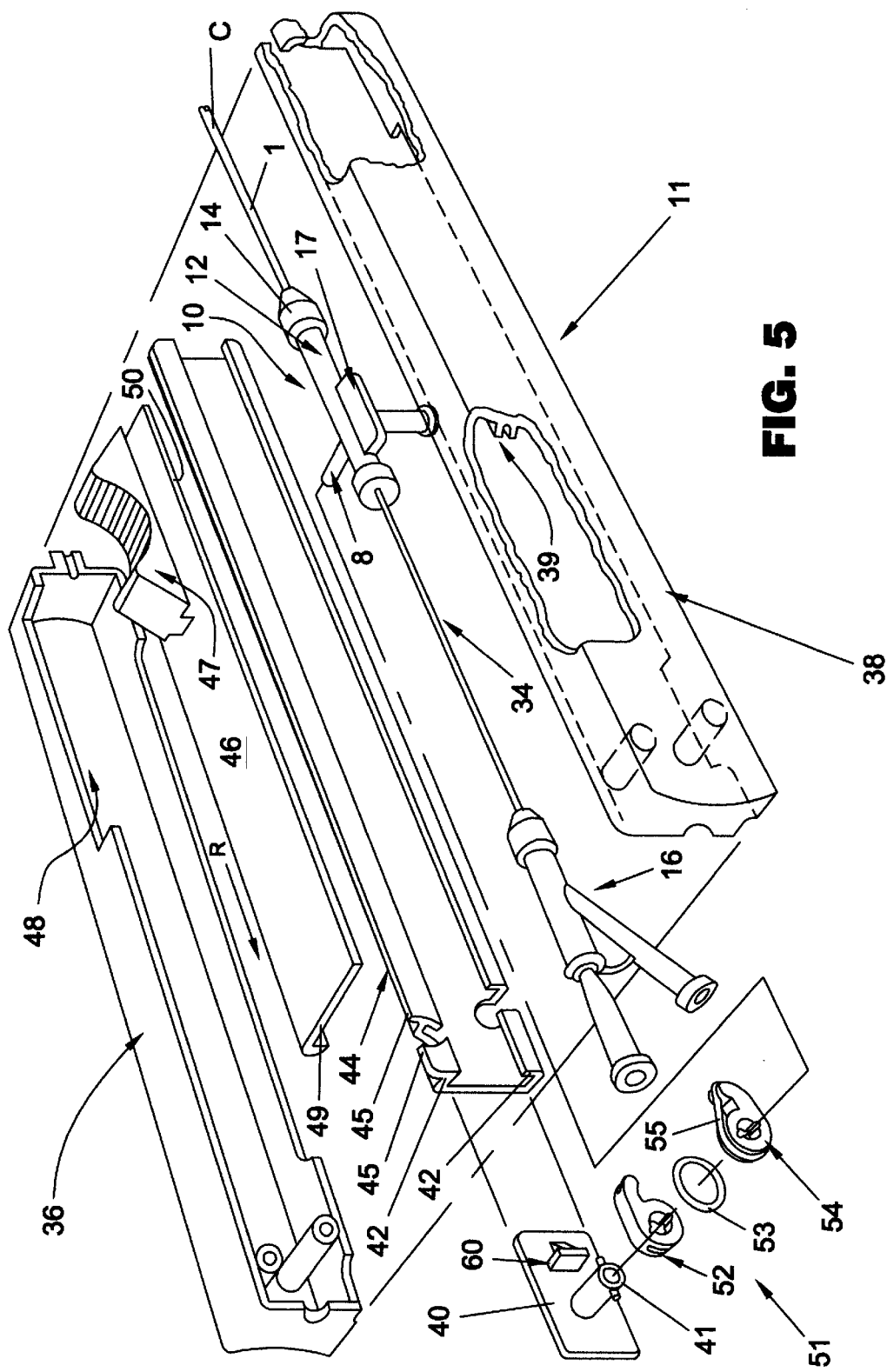
FIG. 5 is an exploded perspective view of a first embodiment of a sheath retractor mechanism and instrument in accordance with the present invention including the portions shown in FIG. 3.

Referring now particularly to FIGS. 3–5, in the illustrated embodiment according to the invention, the sheath retraction mechanism and instrument includes a movable fitting support assembly, generally designated by a reference numeral 10, to which the sheath 1 is affixed. The fitting support assembly 10 has a tubular main body 12 which forms a connector and support with an enlarged front end portion 14 to which the rear end of the plastic sheath 1 is secured and supported, for example, with adhesive. The catheter tube C loosely passes entirely through the bore of the connector conduit 12 and extends rearwardly into a Y-connector or support fitting generally designated 16 which has a main tubular body 18 through which the catheter C extends and is fixed, for example, by adhesive 19 adjacent the rear fluid coupling end 20. As shown in FIG. 3, the fitting support assembly 10 is movable, as indicated by arrow R, when the sheath 1 is retracted, so that it moves toward the Y support fitting 16.

The fitting 16 has a fluid coupling end 20, which provides fluid communication from the saline supply and control (not shown) for the inflation and deflation of the balloon B through the catheter C. As shown in FIG. 4a, the dual lumen catheter C has a generally central lumen 22 which provides passageway for a guide wire (not shown) which is passed through the patient's vascular lumen as a pilot to provide smooth guidance of the catheter C and sheath 1 through the vascular lumen to the catheterization and implantation site. The offset lumen 24 serves as the flow conduit for the delivery of saline or other fluid to the balloon for inflation. The balloon inflation lumen 24 has a lateral vent aperture 26, FIG. 4a, which is located to communicate with the angular leg conduit 28 for venting saline discharge from the balloon catheter.

Referring again to FIG. 4, the forward end of the tubular conduit 18 of fitting 16 has an enlarged, threaded coupling 28 which internally seats an annular, elastomeric compression packing 30 through which the catheter C passes and is circumferentially supported. An external retaining nut 32 is threaded onto the coupling 28 and concentrically secures the rear end of a rigid tube 34 which reinforces the portion of the catheter C projecting therethrough, and extending between fitting 10 and the Y-connector 16. The rigid tube 34 extends to or passes through the fitting and support assembly 10 when retracted with the sheath 1.

Figure 12:
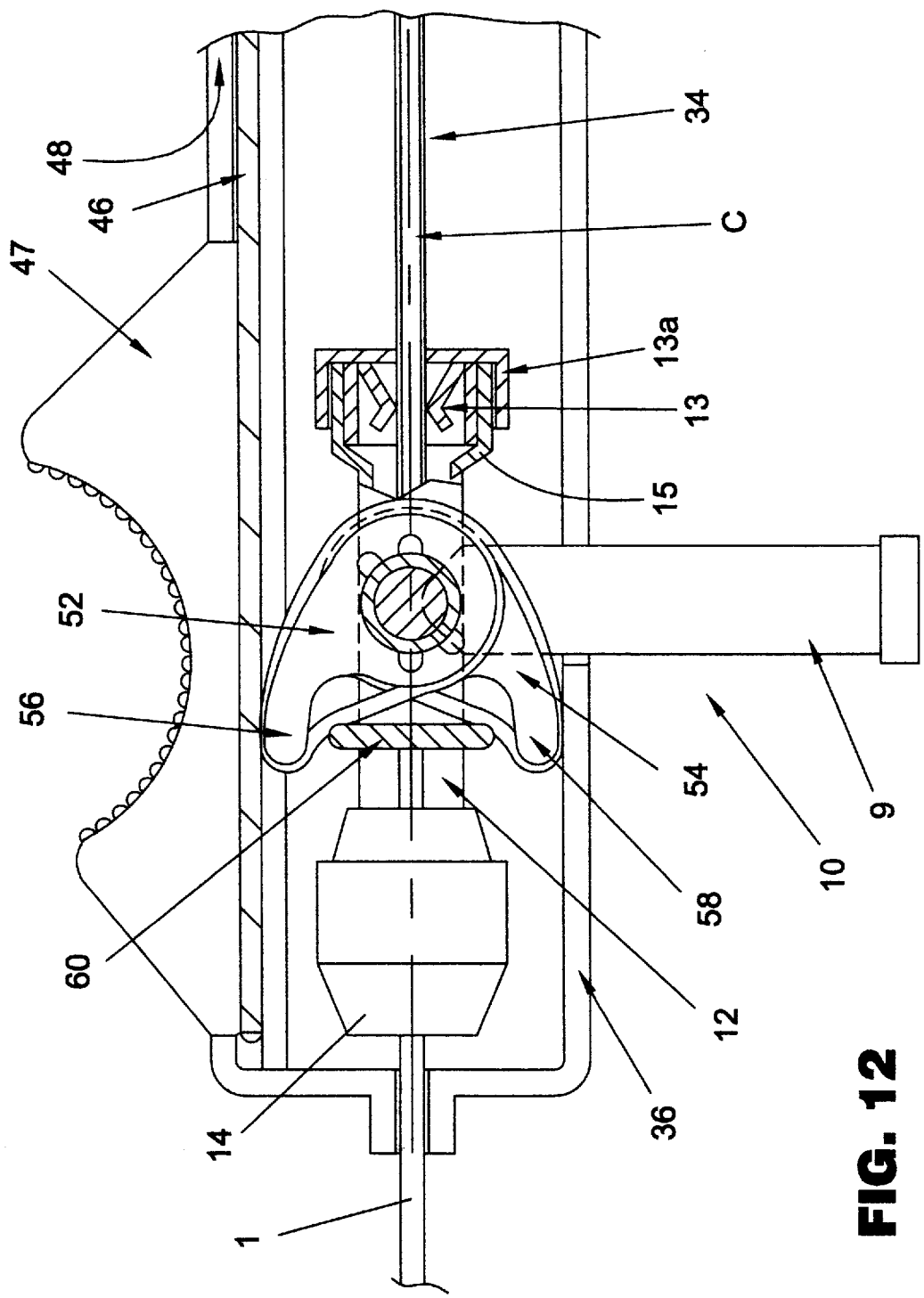
FIG. 12 is an enlarged, further sectional view of the instrument portion shown in FIG. 11.

As shown in FIGS. 3, 5 and 12, the sheath 1 is larger in diameter than the rigid tube 34, such that the tube 34 is slidable entirely through the main conduit tube 12 of the T fitting support assembly 10 so that the rigid tube 34 will pass into the sheath 1 when the sheath is retracted with the assembly 10 moved toward the Y fitting 16 as shown in FIG. 3 and more filly described hereinafter with regard to FIGS. 13–18. As particularly shown in FIG. 12, the enlarged rear end portion 15 has an annularly folded shaft seal 13 fitted therein to provide, for example, a 10–20 psi fluid seal with low sliding friction against the rigidizing tube 34 in the relative translation therebetween. The seal 13 prevents any leakage along the rigidizing tube 34 when body fluid such as blood are flushed and discharged through the lateral connecting conduit 9 communicating from the main conduit 12.

Referring again to FIG. 5 and FIGS. 8 and 9, it should be noted that the orientation of the components 10 and 16 are reversed from FIG. 3. The support fitting 10 and Y-connector 16 are mounted within an operating housing including split or halved portions 36 and 38 which engage and hold the rear, Y-connector assembly 16 stationary while allowing rearward movement only of the forward fitting assembly 10 and the attached sheath 1 toward the stationary Y-connector or fitting assembly 16 in the illustrated embodiment. The Y-connector or fitting assembly 16 is clamped between the split housing portions 36 and 38. The fitting assembly 10 with sheath 1 affixed is mounted to a movable sliding plate 40 which is slidable mounted within, opposed guiding grooves 42 formed in an elongate track 44 installed within the housing portion 36.

As shown in the sectional view of FIG. 10, an operating, drive slide 46 spans the upper walls of the housing portions 36 and 38 and has an upwardly projecting finger engagement boss 47 projecting through a slot 48 formed between the walls of the housing portions 36 and 38. The slide 46 also has a downwardly extending retaining web 49 which rides against a guide shoulder 45 formed as the upper portion of the guide track 44. The side edge 50 of the drive slide 46 rides through a supporting groove 37, FIG. 10, in the housing portion 38. The fitting assembly 10 has a lateral guide blade 17, FIG. 7, which slides through a second groove or guide slot 39 formed into the side wall of the housing portion 38.

As will become clear from the description to follow, the slide plate 40 is affixed to the fitting 10, and carries drive coupling structure, designated generally 51. The drive coupling structure serves to effect operative interconnection of the slide plate 40 to the drive slide 46. As such, as the drive slide 46 is moved rearwardly, arrow R, a positive coupling is attained and the slide 40, fitting 10 and sheath 1 are retracted. When the slide 46 is moved in the opposite or forward direction, arrow F, the drive coupling structure 51 is disengaged from the slide 46, and no forward movement of the slide plate 40, fitting 10, or sheath 1 is produced. Thus, the slide plate 46 can be moved in the direction of arrow R to obtain an incremental retraction of sheath 1, and then moved in the direction of arrow F to in effect reset the drive slide 46; for the next incremental step of movement of the sheath 1 in the rearward or retractive direction. Due to the de-coupling of the drive coupling structure 51 upon forward movement of the drive slide 46, arrow F, this movement does not result in forward movement of the sheath 1.

The fitting assembly 10 has a lateral coupling pin 8 received in and secured to a receptive coupling tube 41 projecting from the slide plate 40. The tube 41 also forms a pivotal bearing on which two grip and release, transmission pawls 52 and 54 of the drive coupling structure 51 are mounted side by side for pivot thereon in the sheath retraction operation as described hereinafter. The coupling tube 41 has a pair of laterally projecting retainer pins 43 which pass through mounting slots 39 formed into each of the pawls 52,54 during mounting onto the tube 41 in assembly. The pawls 52 and 54 each have respective traction arms 56 and 58 which project eccentrically as shown in FIGS. 11 and 12.

In the illustrated embodiment and referring particularly to FIGS. 6, 7 and 12, each of the pawls 52 and 54 is peripherally grooved to seat a respective elastomeric band or o-ring 53,55 which circumscribes the respective eccentrically-shaped pawl body. The purpose and function of the elastomeric bands 53 and 55, will become apparent.

Referring again to FIGS. 5–7, the slide plate 40 has a laterally projecting biasing lug 60 which is located between the mounted pawl traction arms 56 and 58 as best shown in FIG. 11. The lug 60 engages and tensions the respective elastomeric bands or rings 53 and 55 which also results in a biasing force pushing the traction arms 56 and 58 apart so that the upper traction arm 56 and the uppermost o-ring traction portion 57 is biased to engage the bottom surface of the slide 46, and correspondingly, the lowermost seated o-ring or band traction portion 59 seated on the arm 58 of the pawl 54 is biased to engage the bottom wall 35 of the housing portion 36 as best shown in FIG. 11.

The operation of the drive coupling structure 51 can probably best be understood with reference to FIGS. 11 and 12. When fully assembled, the lug 60 tensions the elastomeric bands 53 and 55 and forces the pawls 52 and 54 to pivot in opposite directions to engage the drive slide 46 and the bottom wall 35 of the housing. This engagement is not directed by the pawls 52 and 54, but rather by these respective traction bands 53 and 55 carried by arms 56 and 58.

It should be noted that alternative arrangement to the bands 53 and 55 can be employed in that the pawls may be provided with friction surfaces, and a spring or some other form of biasing element used to force the pawls into engagement with the drive slide 46 and surface 35, see FIGS. 19 and 20 as discussed hereinafter.

In operation, the pawl 52 is biased clockwise into engagement with drive slide 46, as viewed in FIGS. 11 and 12, while the pawls 54 is biased in a counter-clockwise direction into engagement with the surface 35 of the housing. The traction band portion 57 on pawl 52 grips the underside of slide 46, as such when the drive slide 46 is moved rearwardly as indicated by arrow R, the friction between the slide 46 and traction portion band 57 causes the pawl 52 to pivot further in the clockwise direction increasing the grip force. Correspondingly, when the slide 46 is moved in the direction R, the grip force between the pawl 54 and surface 35 releases permitting the fitting 10 to move to the right as viewed, or rearwardly with the drive slide 46. It will be recalled that movement of the fitting 10 also produces movement of the sheath 1.

When movement of the finger impellor 47 on drive slide 46 is effected in the direction opposite to the arrow R, that is in the forward direction, an opposite reaction takes place more specifically, the pawl 52 will tend to move in the counter-clockwise direction, releasing the friction grip of drive slide 46, permitting the drive slide to move relative to fitting 10. Correspondingly, the lower pawl 54 is also moved counter-clockwise to increase its friction grip on surface 35. The net effect is the drive slide 46 can move to the left as viewed, while the fitting 10 and sheath 1 remain fixed.

Figure 13:
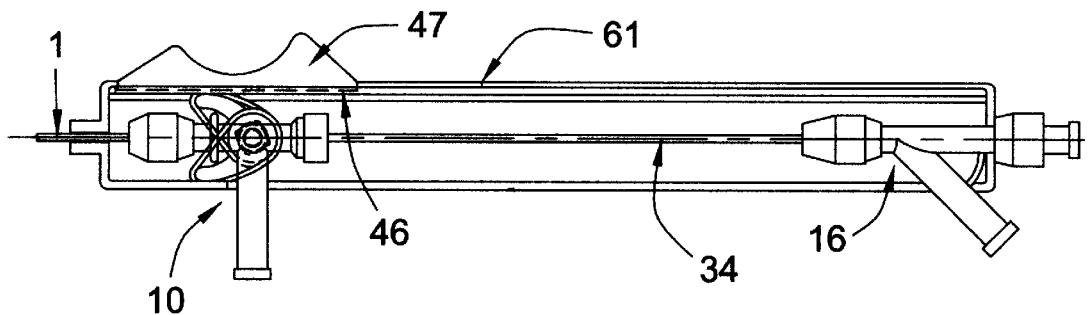
FIGS. 13–18 are internal views of the instrument shown in FIGS. 5–12 illustrating sequential operating steps for the instrument to attain sheath retraction in accordance with the structure and method of the present invention.
Figure 14:
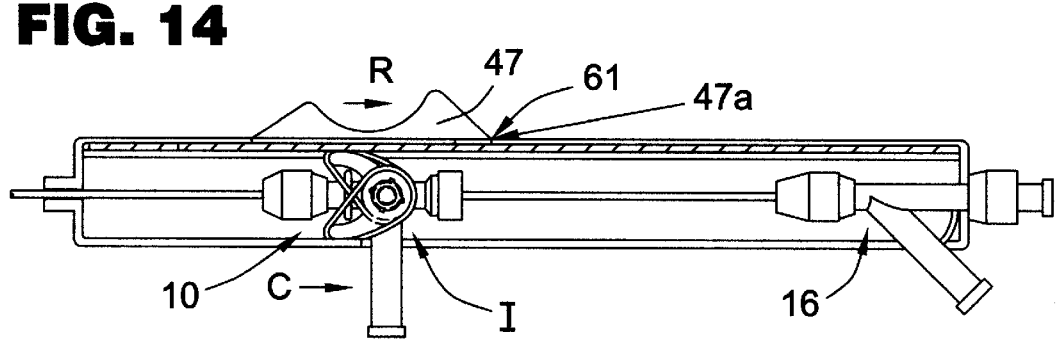

The function and overall operation of the drive coupling structure 51, slide 46 and the pawls 52 and 54 can best be appreciated from a discussion of the operation of the device or instrument 11. As such, the sheath retraction operation of the instrument 11 will now be explained with reference to FIG. 5 and FIGS. 13–18. After previously guiding and precisely locating the balloon/stent B/A and protective sheath 1 through the patient's vascular pathway to the angioplasty implantation site as explained hereinabove with reference to FIGS. 2 and 3, the fitting support assemblies 10 and 16 are in the relative positions generally adjacent the ends of the instrument 11 as shown in FIG. 13, with the sheath 1 projecting leftwardly as illustrated and overlying the stent A. To begin the sheath retraction for exposure of the stent A, which remains stationary at the precise site for subsequent expansion and implantation, the finger impellor 47 and slide 46, arrow R, are moved to the right, as indicated in FIG. 14 (and in FIG. 11). This causes the fitting support assembly 10 to move to the right to the position shown in FIG. 14, and carries or retracts the secured sheath 1 in displacement therewith, equal to the extent of movement. Since the o-ring traction portion 57 grips the bottom surface of the slide 46 and is carried by static friction therewith to the right, the upper pawl 52 will tend to slightly pivot clockwise and further force the o-ring traction portion 57 against the bottom surface of the slide 46 thus increasing the pressure and grip of the entire support assembly 10 thereagainst. At the same time, the grip of the lower o-ring traction portion 59 against the surface of the bottom wall housing portion 35 will tend to loosen with the initial frictional pivot of the lower pawl 54 also in clockwise direction and this will result in release of the grip therebetween so that the strength and grip of the upper o-ring traction portion 57 permits the entire assembly 10 to be carried with the slide 46 to the right as shown in FIG. 14.

The translation or movement to the right of the fitting support assembly 10 and sheath 1 is terminated, however, when the rear edge 47a of the impellor 47 reaches abutment against the stop edge 60 of the upper housing wall slot 48. At this point, the first incremental sheath retraction displacement is defined by the same one-to-one displacement or movement of the finger impellor 47, the fitting support assembly 10, and the attached sheath 1 as represented in FIG. 14.

Figure 15:
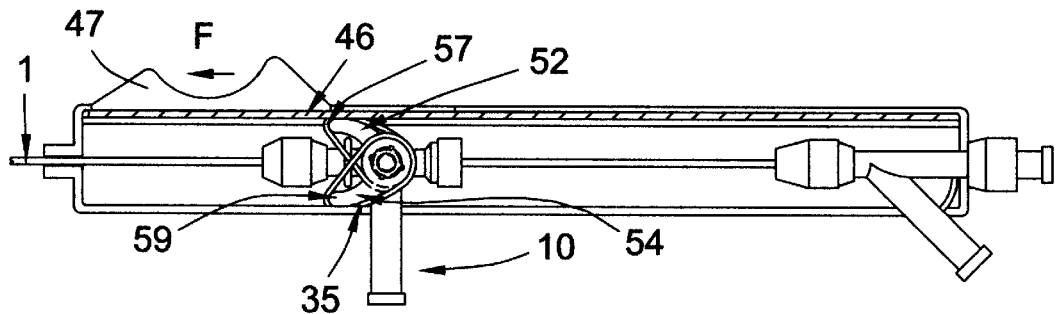

In order to continue and extend the sheath retraction, the finger impellor 47 must be returned to its initial position, as shown in FIG. 15, without, however, advancing the displacement of the fitting support assembly 10 since the secured sheath 1 must not be advanced, only retracted to ensure that the stent position is not disturbed or deflected from the vascular site for implantation. Accordingly, when the finger impellor 47 is manually reversed, as shown in FIG. 15, arrow F, the drive coupling structure 51 is deactivated or releases its grip or drive slide 46. This d-coupling is allowed due to the fact that the grip of the o-ring traction portion against the bottom surface of the slide 46 will be loosened by the momentary tendency for counterclockwise pivot of the upper pawl 52 so that this grip will be swiftly released whereas in contrast, at the same time, the grip of the o-ring traction portion 59 against the surface of the lower housing wall 35 will be strengthened by frictional tendency of the lower pawl 54 to slightly pivot counterclockwise. The combination of the release of the slide 46 by the upper pawl 52 and the strengthened grip by the lower pawl 54 insures that the fitting support assembly 10 remains stationary in position to maintain the retracted position of the sheath 1 and preclude forward movement of the sheath 1, even while the finger impeller 47 is reversed in displacement to the position shown in FIG. 15.

Figure 16:
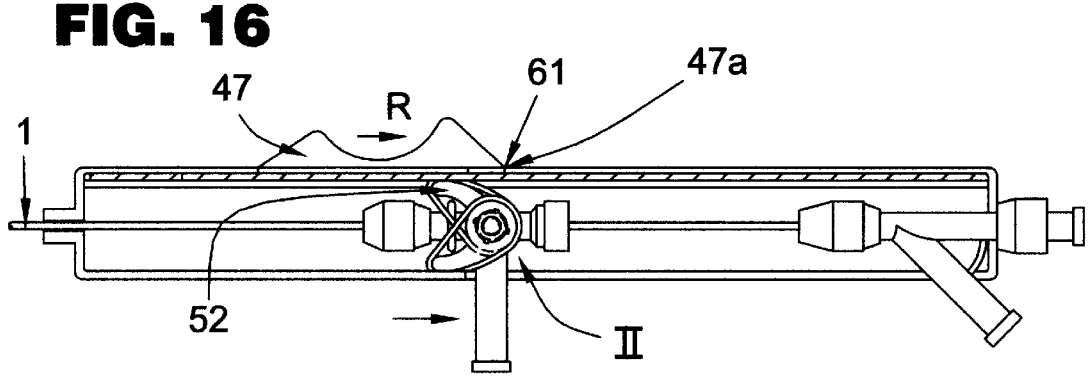
Figure 17:
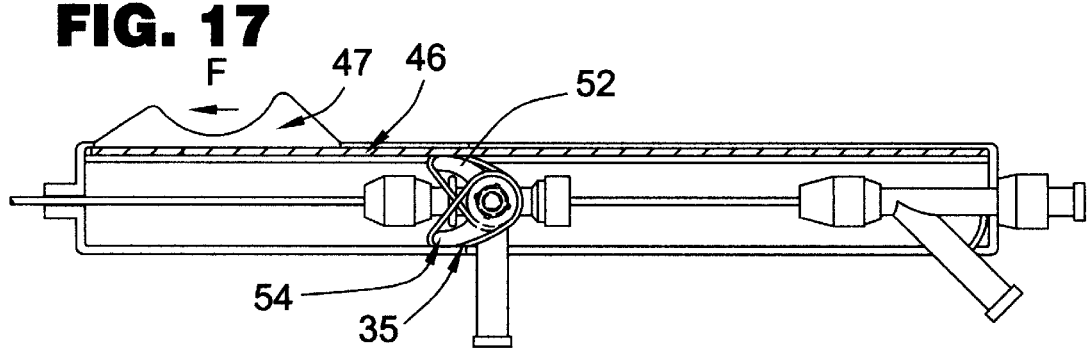

To achieve a second incremental retraction of the sheath 1 and assembly 10 from the position shown in FIG. 15 to the position shown in FIG. 16, the impellor 47 is again displaced rearwardly in the direction of arrow R to drive the slide 46 and the pawl (52)-gripped assembly 10 to the second incrementally displaced position II as shown in FIG. 16 at which the rearward motion of the impellor 47 is again terminated by abutment of the end 47a against the stop 60. Thereafter, as shown in FIG. 17, the impellor 47 and slide 46 are again displaced forwardly in the direction of arrow b, while the assembly 10 remains stationary by release of the pawl 52 from the slide 46 and the anchoring grip of the lower pawl 54 against the bottom wall 35 of the housing.

Figure 18:
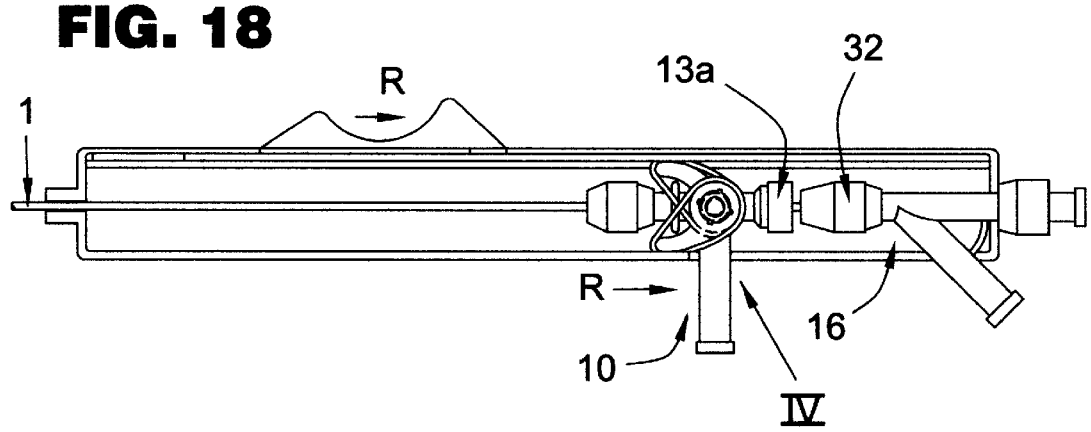

Referring now to FIG. 18, after two additional incremental displacements of the support assembly 10 and sheath numeral 1, driven by the rearward and forward cycling displacement of the impeller 47, the assembly 10 reaches the terminal position designated IV at which the shaft seal cover 13a on the enlarged rear end 15 of the assembly 10 reaches abutment against the retaining nut 32 on the front end of the fitting assembly 16 (for simplicity, a third incrementally retracted position of the assembly 10 has not been illustrated). In the terminal position IV shown in FIG. 18, the sheath 1 is fully retracted to expose the stent "A" as shown in FIG. 3, so that the stent A can then be implanted in the vascular wall D by the balloon expansion procedure.

The one-way incremental retractions of the sheath 1 and fitting assembly 10 are co-extensive with each rearward stroke of the slide 46 so that the operator senses visual and tactile measure of retraction in controlled uniform displacements which eliminate uncertainty in the length of retraction and prevents too swift retraction and any whipping of the catheter's stent-mounted balloon end.

Referring now to FIGS. 19 and 20, a modified embodiment of a sheath retraction mechanism and instrument in accordance with the invention is shown. In this embodiment, the elastomeric bands have been replaced by spring biased pawls 152 and 154 having an alternative means for engaging and releasing the frictional forces. More specifically, the eccentrically projecting traction arms 156 and 158 of the respective pivotal pawls 152 and 154 are fitted with respective gripping pads 160 and 162 fabricated from rubber or similar frictional gripping material. A coil spring 164 or some other form of biasing means is mounted between the two traction arms 156 and 158 which seat opposite ends of the spring 164. This arrangement of the spring 164 provides biasing to force the traction arms 156 and 158 apart so that the rubber pad 160 on the upper traction arm 156 is pressed into frictional engagement against the bottom of the drive slide 146 and the lower pad 162 is pressed to frictionally engage the bottom wall 135 of the housing portion 136 so that the pawls 152 and 154 operate in the grip and release cycle similar to those of the first embodiment and the one-way sheath retraction operation corresponds as hereinabove described with reference to FIGS. 13–18.

Additionally, as illustrated in FIG. 20, the upper traction arm 156 engaged with the drive slide 146 has an extension 157 and terminal foot 159 extending toward the bottom of the slide 146 and normally slightly spaced a distance S therefrom. The foot 159 of the traction arm extension 157 will immediately contact the bottom of the slide 146 to prevent any tendency of the upper pawl 152 and arm 156 toward pivotal rocking with any slight, undesirable forward movement of the sheath at a transition when the slide 146 is moved forwardly after each retracting translation of the fitting support 110 and the sheath 1 in the operation correspondingly described with reference to FIGS. 13–18. In the modified, second embodiment illustrated in FIGS. 19 and 20, a complete circular finger loop 166 serves as the manual drive impellor secured to the slide 146, and a similar ring (not shown) is provided on the housing for stationary grasp relative to the motion of the loop 166.

While a preferred embodiment of the present invention is shown and described, it is envisioned that those skilled in the art may devise various modifications and equivalents without departing from the spirit and scope of the appended claims.

The invention claimed is:

1. A method for particularly retracting a protective sheath from a portion of an elongate member inserted through the sheath, comprising the following steps:

a) activating a drive structure to simultaneously couple said drive structure to said sheath and drive translation of said coupled sheath relative to said elongate member to expose a portion thereof covered by said sheath prior to said translation; and b) repeating step a) to further translate said sheath and expose a further portion of said elongate member, in order to produce sequentially extended exposure of said elongate member by the repetitive sheath translations.

2. A method according to claim 1, wherein step (a) comprises translating said drive structure coupled to said sheath.

3. A method according to claim 1, further comprising uncoupling said drive structure from said sheath.

4. A method according to claim 2, further comprising additional steps comprising uncoupling said drive structure from said sheath; reversely translating said drive structure in a direction opposite to said translating; and recoupling said drive structure to said sheath preparatory to said repetitive step (b) in order to ensure only one-way retracting motion of said sheath.

5. A method according to claim 1, wherein said step (a) comprises engaging respective frictionally adhering surfaces of said drive structure and a coupling structure secured to said sheath.

6. A method according to claim 5, further comprising pressuring said respective adhering surfaces to ensure sufficient adhesion thereof to enable said translation in step (a).

7. A method according to claim 5, further comprising reversely translating said drive structure in a direction opposite to said translating while sliding said drive structure surface against said coupling structure surface to prevent reversely translating said sheath with said drive structure.

8. A method according to claim 7, further comprising holding said coupling structure stationary during said reversely translating said drive structure in order to ensure only one-way retracting motion of said sheath.

9. A method for particularly retracting a protective sheath from a portion of an elongate member movably inserted through the sheath, comprising the following steps:
 a) coupling a drive structure to said sheath;
 b) driving translation of said sheath relative to said elongate member to expose a portion thereof covered by said sheath prior to said driving;
 c) uncoupling said drive structure from said sheath;
 d) reversely translating said drive structure in a direction opposite to translation in step (b);
 e) recoupling said drive structure to said sheath; and
 f) repeating step (b) to further translate said sheath and expose a further portion of said elongate member, in order to produce sequentially extended exposure of said elongate member by the repetitive sheath translations.

10. An actuating mechanism for translating a sheath member relative to an elongate member inserted through the sheath member, comprising:
 a drive structure;
 a coupling structure coupleable to said sheath member and constructed to enable selective coupling of the coupling structure to said drive structure in order to drive translation of the coupled sheath member in one or more translation increments and to enable selective uncoupling of the drive structure from said coupling structure following each said translation increment.

11. An actuating mechanism according to claim 10, wherein said coupling structure comprises a frictional coupling element arranged for gripping engageability of said drive structure.

12. An actuating mechanism according to claim 10, wherein said coupling structure comprises a pivotal pawl element biased to grip said drive structure.

13. An actuating mechanism according to claim 10, wherein said coupling structure comprises a first grip member arranged to releasibly grip said drive structure to enable said selective coupling thereof, and a second grip structure arranged to enable releasable gripping of an adjacent non-moving surface in said mechanism in order to promote release of said coupling grip by said first grip member and prevent reverse translation of said sheath member in a direction opposite to said translation increment when said drive structure is reversibly translated.

14. An actuating mechanism according to claim 13, wherein said first and second grip members comprise respective first and second pivotal pawl members pivotally mounted on a support structure connectable to said sheath member.

15. An actuating mechanism according to claim 14, wherein said support structure includes a tubular portion through which said elongate member is extendable to enable relative translation of said sheath member relative thereto.

16. An actuating mechanism according to claim 14, wherein each of said first and second grip members comprises a frictional gripping portion.

17. An actuating mechanism according to claim 10, wherein said coupling structure is secured to a support structure connectable to said sheath member.

18. An actuating mechanism according to claim 17, wherein said coupling structure is further secured to a guide member spaced from said support structure and arranged to guide said retraction.

19. An actuating mechanism according to claim 17, wherein said coupling structure includes a resilient biasing member arranged to bias said selective coupling.

20. An actuating instrument for particular use in retracting a protective sheath member relative to a catheter movably inserted through the sheath member, said instrument comprising:
 a support structure connectable to said sheath member to support said retraction thereof;
 a drive member arranged to propel retraction of said support structure to enable the retraction of the sheath member therewith; and
 a coupling structure affixed to said support structure and constructed to enable selective coupling of said coupling structure to said drive member in order to drive said retraction in one or more retraction increments and to enable selective uncoupling of said coupling structure from said drive member following each of said retraction increments.

21. An instrument according to claim 20, wherein said drive member is reversibly movable in order to propel retraction of said support structure said in a first movement direction of said drive member;
 said drive member being arranged to enable a second directional movement uncoupled from said support structure in a direction opposite to said first movement direction, in order to propel retraction of said sheath member in one or more retraction increments of one-way displacement, so that successive retraction increments of said sheath member are alternated by uncoupled opposing movements of said drive member relative to said increments of retraction.

22. An instrument according to claim 20, wherein said drive member is reversibly translatable in opposing directions respectively corresponding to said selective coupling and uncoupling.

23. An instrument according to claim 20, wherein said drive member is arranged to propel said support structure in coextensive displacement therewith defining said retraction increments of said support structure and sheath member.

24. An instrument according to claim 20, further comprising stop structure contactable against said drive member to terminate propelling motion of said drive member thereagainst in a first movement direction to define a displacement dimension of said retraction increments.

25. An instrument according to claim 20, wherein said support structure includes a tubular portion through which said catheter is extendable to enable retraction of said support structure and sheath member relative thereto.

26. An instrument according to claim 25, further comprising a second support structure connectable to said catheter to support the extension of said catheter through the sheath support structure.

27. An instrument according to claim 26, wherein said second support structure comprises a rigid tube through which said catheter is extendable for support during retraction of the sheath support structure thereover.

28. An instrument according to claim 27, wherein said sheath support structure comprises a seal member sealable on said rigid tube to prevent any leakage of bodily or other fluid from between said sheath support structure and said rigid tube extendable therethrough.

29. An instrument according to claim 20, wherein said coupling structure comprises a frictional coupling element arranged for gripping engagement of said drive member.

30. An actuating instrument according to claim 20, wherein said coupling structure comprises a first grip member arranged to releasibly grip said drive member to enable said selective coupling thereof, and a second grip member arranged for gripping a stationary, anchor structure in said instrument in order to promote release of said coupling grip by said first grip member and prevent translation of said sheath member in a direction opposite to said retraction thereof.

31. An instrument according to claim 30, wherein each of said first and second grip members comprises a frictional gripping portion.

32. An instrument according to claim 30, wherein said first and second grip members comprise respective first and second pivotal pawl members pivotally mounted on said support structure connectable to said sheath member.

33. An instrument according to claim 32, wherein said first and second pivotal pawl members are arranged in opposing bias against said respective drive member and anchor structure.

34. An instrument according to claim 33, wherein a spring member is seated on both of said first and second pawl members imposing said opposite bias thereon respectively.

35. An instrument according to claim 30, wherein said drive member comprises a reversibly translatable member releasibly gripped by a first frictionally engaged pivotal grip member of said coupling structure, and said anchoring structure comprises a stationary wall of said instrument with respective to said translation of said sheath support structure, said stationary wall releasibly gripped by a second frictionally engaged pivotal grip member of said coupling structure.

36. An instrument according to claim 30, wherein said coupling structure is secured to said support structure for retraction therewith.

37. An instrument according to claim 36, wherein said coupling structure is further secured to a guide member spaced from said support structure and arranged to guide said retraction.

38. A method for particularly retracting a protective sheath from a portion of an elongate member, comprising the following steps:
a) coupling a drive structure to said sheath;
b) activating said drive structure to drive translation of said coupled sheath relative to said elongate member to expose a portion thereof covered by said sheath prior to said translation;
c) uncoupling said drive structure from said sheath; and
d) repeating step (b) to further translate said sheath and expose a further portion of said elongate member, in order to produce sequentially extended exposure of said elongate member by the repetitive sheath translations.

39. A method for particularly retracting a protective sheath from a portion of an elongate member, comprising the following steps:
a) coupling a drive structure to said sheath;
b) translating said drive structure coupled to said sheath to drive translation of said coupled sheath relative to said elongate member to expose a portion thereof covered by said sheath prior to said translation; and
c) uncoupling said drive structure from said sheath in order to ensure only one-way retracting motion of said sheath;
d) reversely translating said drive structure in a direction opposite to said translating in step (b);
e) recoupling said drive structure to said sheath; and
f) repeating step (b) to further translate said sheath and expose a further portion of said elongate member, in order to produce sequentially extended exposure of said elongate member by the repetitive sheath translations.

40. A method for particularly retracting a protective sheath from a portion of an elongate member comprising the following steps:
a) engaging respective frictionally adhering surfaces of a drive structure and a coupling structure secured to said sheath to couple said drive structure to said sheath;
b) activating said drive structure to drive translation of said coupled sheath relative to said elongate member to expose a portion thereof covered by said sheath prior to said translation;
c) reversely translating said drive structure in a direction opposite to said translating in step (b) while sliding said drive structure surface against said coupling structure surface to prevent reversely translating said sheath with said drive structure; and
d) repeating step (b) to further translate said sheath and expose a further portion of said elongate member, in order to produce sequentially extended exposure of said elongate member by the repetitive sheath translations.

41. A method according to claim 40, further comprising holding said coupling structure stationary during said reversely translating said drive structure in order to ensure only one-way retracting motion of said sheath.

* * * * *

UNITED STATES PATENT AND TRADEMARK OFFICE
CERTIFICATE OF CORRECTION

PATENT NO. : 5,868,755
DATED : February 9, 1999
INVENTOR(S) : Rowland W. Kanner and Larry Lee Young It is certified that error appears in the above-identified patent and that said Letters Patent is hereby corrected as shown below:

Column 4, Line 49 "filly" should be -- fully --

Column 9, Line 35 "to translation" should be -- to said translation --

Signed and Sealed this

Twenty-seventh Day of July, 1999

Attest:

Q. TODD DICKINSON

Attesting Officer

Acting Commissioner of Patents and Trademarks